(12) United States Patent
Eriksen et al.

(10) Patent No.: US 6,409,671 B1
(45) Date of Patent: Jun. 25, 2002

(54) ULTRASONOGRAPHY

(75) Inventors: Morten Eriksen, Oslo; Sigmund Frigstad, Trondheim, both of (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/597,726

(22) Filed: Jun. 19, 2000

Related U.S. Application Data

(63) Continuation of application No. PCT/GB98/03809, filed on Dec. 17, 1998.
(60) Provisional application No. 60/071,713, filed on Jan. 16, 1998.

(30) Foreign Application Priority Data

Dec. 18, 1997 (GB) .............................................. 9726773

(51) Int. Cl.$^7$ ................................................ A61B 8/00
(52) U.S. Cl. ....................................................... 600/458
(58) Field of Search ................................ 600/437, 443, 600/458, 454–456; 424/9.51, 9.52

(56) References Cited

U.S. PATENT DOCUMENTS

| | | | |
|---|---|---|---|
| 4,567,898 A | | 2/1986 | Plugge et al. |
| 5,255,683 A | * | 10/1993 | Monaghan .................. 600/458 |
| 5,419,328 A | * | 5/1995 | Goh et al. .................. 600/443 |
| 5,601,085 A | | 2/1997 | Ostensen et al. |
| 5,664,571 A | | 9/1997 | Yamazaki |
| 5,749,364 A | * | 5/1998 | Sliwa, Jr. et al. ........... 600/438 |
| 6,086,539 A | * | 7/2000 | Guracar et al. ............. 600/443 |

FOREIGN PATENT DOCUMENTS

| WO | WO 94 28939 A | 12/1994 |
|---|---|---|
| WO | WO 96 33655 A | 10/1996 |
| WO | WO 97 29783 A | 8/1997 |

* cited by examiner

*Primary Examiner*—Francis J. Jaworski
(74) *Attorney, Agent, or Firm*—Royal N. Ronning, Jr.; Robert F. Chisholm; Stephen G. Ryan

(57) ABSTRACT

Local aberrations in the perfusion and/or compliance of vasculated tissue may be detected by contrast agent-enhanced ultrasound imaging procedures wherein a sequence of ultrasound image data is generated in respect of a region of interest in vasculated tissue, the image data is processed to generate waveforms representative of arterial pulsatility, and these waveforms are analyzed for variations such as phase distortions which are characteristic of local aberrations in tissue perfusion and/or compliance.

18 Claims, No Drawings

ULTRASONOGRAPHY

This application is a continuation of co-pending PCT application number PCT/GB98/03809, filed Dec. 17, 1998 (of which the entire disclosure of the pending, prior application is hereby incorporated by reference), which itself is a continuation-in-part of application No. 60/071,713, filed Jan. 16, 1998.

This invention relates to ultrasound imaging, more particularly to use of contrast agent-enhanced ultrasound imaging in the detection of local aberrations in perfusion and/or compliance of vasculated tissue.

Measurements of tissue perfusion, i.e. blood flow per unit of tissue mass, are of value in, for example, detection of regions of low perfusion, e.g. as a result of arterial stenosis, and in detection of abnormal growths such as tumours in tissues such as the liver, kidney, thyroid, prostate, testes and breast, tumour tissue typically having different vascularity from healthy tissue. Measurement of cardiac perfusion in order to identify any myocardial regions supplied by stenotic arteries is of particular importance.

Currently used methods for obtaining quantitative perfusion data utilise radioisotopic imaging techniques such as scintigraphy, positron emission tomography and single photon emission computed tomography. These techniques all involve injection of radioactive substances, with potential safety risks for both the patient and medical staff, and use of expensive imaging equipment; this inevitably prohibits their widespread use.

Ultrasound imaging is a relatively inexpensive and essentially non-invasive imaging technique which is increasingly used for diagnostic purposes. However, whilst ultrasound images, particularly images obtained using ultrasound contrast agents, may provide qualitative information as to whether particular organs or regions thereof are perfused or not, they do not readily permit quantification of levels of perfusion. In part this is because reduced perfusion is not necessarily accompanied by detectable vascular volume changes which would give rise to perfusion-related variations in the intensity of the backscattered ultrasound signal. Quantification of contrast agent concentration in a particular tissue region is itself an uncertain process which is inevitably imprecise given that the degree of attenuation of ultrasound irradiation by proximal intervening tissue cannot accurately be determined.

Wash-in kinetic studies following intravenous injection of a contrast agent bolus may in principle give information on tissue perfusion, but in practice the bolus waveforms lack the abrupt temporal changes needed for reliable observations to be made. Moreover, most perfusion changes are accompanied by distribution volume variations which counteract their temporal effect, so that the wash-in kinetics of intravascular tracers cannot give a precise measure of perfusion.

Accurate perfusion measurements with high spatial resolution are also made difficult by the substantial spacial heterogeneity of normally perfused tissue.

A variety of ultrasound Doppler techniques have been proposed for measuring the velocity of blood flow. Thus, for example, U.S. Pat. No. 5,211,169 (Prism Imaging, Inc.) discloses that Doppler signals may be analysed to obtain information in respect of movement of the heart and in respect of the more rapid movement of the blood pool; the latter information is used to determine changes in the size of the blood pool, thereby permitting calculation of heart function parameters such as the ejection fraction. Contrast agents are not used in this technique, return signals from the blood pool being generated by backscatter from red blood cells.

Similar Doppler velocity measurements may be used to detect tissue regions with reduced perfusion. Interpretation of the Doppler waveform must be made in such a way as to eliminate the effects of local anatomical detail such as vessel size and orientation, for example by calculating dimensionless indices such as the "resistance index", "Pourcelot index" or "pulsatility index" by simple waveform analysis techniques. Analysis of these may permit detection of abnormal circulation on the basis that arterial pulsatility waveforms are different upstream and downstream of an arterial stenosis, thus the waveform undergoes characteristic changes when arterial resistance is increased, both as a result of the resistance changes per se and because the pressure distal to the stenosis causes increased local compliance through non-linear elastic mechanisms. In general, the arterial velocity pulsation waveform in a stenotic vessel is determined by factors such as the input pressure waveform (i.e. the systemic arterial pressure), the resistance of the stenosis, the compliance of vessels between the transducer and the stenosis, and the compliance of the distal vascular bed. The pattern of flow velocity change proximal to a stenosis is characterised by the effects of pulse wave reflection and tends to have a relatively high content of high frequencies, whereas the waveform distal to a stenosis tends to be low-pass filtered and phase shifted by the increased resistance and compliance. Such applications are, however, limited by the need for anatomical identification of the desired vessels, which must be "visible" and non-perpendicular to the irradiating ultrasound beam, and are only practicable in respect of measurements involving relatively large vessels.

The present invention is based on the finding that contrast agent-enhanced ultrasound imaging may be used to identify local aberrations in the perfusion and/or compliance of vasculated tissue by image analysis techniques which identify such aberrations through associated variations in waveforms representative of arterial pulsatility.

Thus according to one aspect of the present invention there is provided a method for detecting local aberrations in the perfusion and/or compliance of vasculated tissue within a human or non-human animal subject pretreated with an intravascularly administered ultrasound contrast agent, said method comprising the steps:

i) generating a sequence of ultrasound image data in respect of a region of interest in said vasculated tissue;

ii) processing said data to generate waveforms representative of arterial pulsatility; and iii) analysing said waveforms for variations characteristic of local aberrations in tissue perfusion and/or compliance.

The invention further provides the use of an ultrasound contrast agent both as and in the manufacture of an image-enhancing composition for administration to the vascular system of a human or non-human animal subject in order to detect local aberrations in perfusion and/or compliance within said vascular system in accordance with the above-defined method.

Representative ultrasound imaging techniques which may be useful in accordance with the invention include fundamental B-mode imaging; harmonic B-mode imaging including reception of sub-harmonics and the second and higher harmonics; power Doppler imaging, optionally including selective reception of fundamental, harmonic or sub-harmonic echo frequencies; power Doppler imaging utilising loss of correlation or apparent Doppler shifts caused by changes in the acoustical properties of contrast agent microbubbles such as may be caused by spontaneous or ultrasound-induced destruction, fragmentation, growth or coalescence; pulse inversion imaging, optionally including selective reception of fundamental, harmonic or subharmonic echo frequencies, and also including techniques wherein the number of pulses emitted in each direction exceeds two; pulse inversion imaging utilising loss of correlation caused by changes in the acoustical properties of contrast agent microbubbles such as may be caused by spontaneous or ultrasound-induced destruction, fragmentation, growth or coalescence; pulse pre-distortion imaging, e.g. as described in 1997 IEEE Ultrasonics Symposium, pp. 1567–1570; ultrasound imaging techniques based on comparison of echoes obtained with different emission output amplitudes or waveform shapes in order to detect non-linear effects caused by the presence of gas bubbles; ultrasound imaging techniques where images are taken at different acoustic output levels such as one with high power and up to ten (e.g. two or three) images are taken at low power; and ultrasound imaging techniques based on comparison of echoes obtained with any of the above mentioned techniques, in order to study spatial and temporal speckle variations after injection of a contrast agent as described in WO-A-9712551, the contents of which are herein incorporated by reference.

The use of power Doppler imaging, i.e. Doppler imaging in which signal intensities in respect of velocities above a certain level are measured, in conjunction with intravascularly administered contrast agents to identify local aberrations in vasculated tissue perfusion and/or compliance represents one advantageous embodiment of the invention. As well as giving a general increase in signal intensity which enables visualisation of blood flow within very small vessels, the presence of contrast agent improves the signal-to-noise ratio, thereby permitting use of a shorter temporal image averaging time constant than is normally employed in power Doppler imaging. This in turn allows the visualisation of waveforms representing arterial pulsatility in perfused tissue, for example as cardiac-synchronous pulsatile flashing patterns. Analysis of such pulsatile patterns to detect the temporal and spatial pattern of variation in the Doppler signal permits significantly more precise detection and imaging of local aberrations in tissue perfusion and/or compliance than do the hitherto used methods based on Doppler velocity waveform indices. Accordingly such embodiments of the invention may be useful in detecting very early arterial stenosis, for example before significant blood flow reduction has occurred or where this is masked by autoregulation, as a result of changes in vascular compliance caused by reduced internal pressure distal to the stenosis. Such embodiments may also be useful in tumour detection since the lack of vascular tissue differentiation in malignant tumour vessels may cause resistance and compliance conditions different from normal tissue.

Other embodiments include the use of imaging techniques such as B-mode imaging, especially harmonic techniques such as second harmonic B-mode imaging. Such techniques may, for example, be used to record arterial pusatility waveforms generated as a result of volume pulsations induced within the vascular system by the cardiac cycle.

A further improvement may be obtained by combining any of the above mentioned techniques with three dimensional acquisition and reconstruction of the ultrasound image, allowing assessment of the three dimensional vessel architecture and vascular state to be performed. Doppler based methods may be used for this purpose, but pulse inversion imaging and harmonic imaging techniques such as second harmonic B-mode imaging may be preferred as they provide excellent spatial resolution and are independent on direction and rate of flow and hence these methods may provide information on vascular geometry and vascular state with excellent resolution containing information of the microcirculation. A further improvement may be obtained in combination with speckle variation analysis and/or tissue background subtraction.

Any appropriate imaging equipment operating in intensity mode may be employed, for example comprising a phased-array sector or linear array ultrasound scanner. In Doppler investigations the tissue movement artefact filter is advantageously set to a relatively high value, and is preferably selected to have characteristics which result in smoothly decreasing signal sensitivity as velocities approach zero; filters having a linear power versus frequency curve are particularly preferred. Such high-pass filtering modulates the intensity of the displayed signal in a linear manner and may generate a pulsatile pattern as arterial blood velocities vary from being above and below the threshold. It is generally preferred that the intensity signal should be processed linearly with no logarithmic compression; such processing may be effected without regard to background tissue echo properties.

In order to enhance the sensitivity of phase shift detection, signal detection is preferably made with respect to a frequency and phase reference, for example derived from an electrocardiogram (ECG) or similar cardiac-synchronous signal. Other natural rhythms such as the respiratory cycle may similarly be used; venous flow velocities are modulated by respiration, as is the sympathetic innervation of perhipheral resistance vessels. Alternatively or additionally, externally applied reference pulses, e.g. with frequencies of up to 100 Hz, may be used; thus, for example, a mechanical vibrator may be positioned above a major artery so as to transmit pressure pulsations into the bloodstream.

Signal processing may be effected by calculating the phase and amplitude of the intensity signal pulsation at the reference frequency or a whole number multiple thereof for each relevant pixel in the image, for example using a Fourier transform; if desired, the image may first be decimated by two dimensional low-pass filtering and re-sampling. If a series of Doppler intensity images ($I_1, I_2 \ldots I_N$) within a cardiac reference cycle are obtained at times $t_1, t_2 \ldots t_N$ and two successive ECG r-wave detection events defining this cycle occur at $T_1$ and $T_2$, then the complex Fourier sum at a given $p^{th}$ harmonic of the heart rate for a given pixel (x,y) can be calculated as $$P_{p,x,y} = \sum_n I_{n,x,y} \exp\left[\frac{j2\pi p(t_n - T_1)}{T_2 - T_1}\right]$$

This calculation may be repeated for a number of successive cardiac cycles, and the resulting Fourier coefficients may be averaged to improve the signal-to-noise ratio. Alternatively, such averaging may be effected for real-time applications by time constant low-pass filtering.

The complex Fourier coefficient may, for example, be used to construct a coloured imaging which may if desired be overlaid on a grey-scale tissue image. Thus, for example, complex values based on Fourier coefficients for the fundamental heart rate frequency (p=1) may be encoded with the absolute value as brightness and the phase as colour (e.g. using a continuous circular rainbow scale). Areas of detectable perfusion will then be more or less bright, whilst regions of compromised circulation will be identified by colour variations indicative of phase distortion. Information contained in higher harmonics of the heart rate frequency (p>1) may additionally or alternatively be used to increase the sensitivity of phase shift detection.

Alternatively, several simultaneous variables may be calculated and used in multivariate statistical tissue characterisation. Representative variables which may be used in this way are the phase and amplitude of the signal at the heart rate or a harmonic thereof, the temporal mean value of the signal intensity and the peak signal intensity during a cardiac cycle.

Techniques such as ECG-gated coherent averaging may be used to build up an accurate map of regional pulsatility for a whole image; if desired, empirical pulsatility indices may be calculated and displayed, for example as a colour overlay image. A reasonable estimate of the coherent averaged cycle may be obtained by reverse Fourier transformation of discrete coefficients for a limited set of values of p or by performing coherent averaging in time domain, compensating for the variable duration of cardiac cycles by time axis interpolation.

As noted above, the method of the invention may be applied to investigations of pathological conditions other than arterial stenoses, for example to detection of tumours in tissues such as the prostate, testes, thyroid, kidneys or breast. The method may also be useful for identifying the origin of the blood supplied to liver lesions, distinguishing between blood supplied from the liver artery (with pulsations) and blood supplied from the portal vein (with minimal pulsation). Vascular supply to skeletal muscle may also be studied, for example to detect impaired circulation caused by an elevated local interstitial pressure, thought to be a pathogenetic mechanism in skeletal muscle pain conditions. Analysis of transcranial images may permit information to be gained in respect of both larger and smaller blood vessels within brain tissue.

The ultrasound contrast agent administered to the subject should be sufficiently stable in vivo to be recirculated in the blood stream following administration, so that it may become equilibrated in the blood pool prior to imaging. Subject to this requirement substantially any ultrasound contrast agent may be employed. Contrast agents comprising or capable of generating dispersions of gas microbubbles are preferred, since such dispersions are particularly efficient backscatters of ultrasound by virtue of the low density and ease of compressibility of the microbubbles.

Any biocompatible gas may be present in such gas dispersions, the term "gas" as used herein including any substances (including mixtures) at least partially, e.g. substantially or completely in gaseous (including vapour) form at the normal human body temperature of 37° C. The gas may thus, for example, comprise air; nitrogen; oxygen; carbon dioxide; hydrogen; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as methylsilane or dimethylsilane; a low molecular weight hydrocarbon (e.g. containing up to 7 carbon atoms), for example an alkane such as methane, ethane, a propane, a butane or a pentane, a cycloalkane such as cyclopropane, cyclobutane or cyclopentane, an alkene such as ethylene, propene, propadiene or a butene, or an alkyne such as acetylene or propyne; an ether such as dimethyl ether; a ketone; an ester; a halogenated low molecular weight hydrocarbon (e.g. containing up to 7 carbon atoms); or a mixture of any of the foregoing. Advantageously at least some of the halogen atoms in halogenated gases are fluorine atoms; thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1,1-difluoroethane and perfluorocarbons. Representative perfluorocarbons include perfluoroalkanes such as perfluoromethane, perfluoroethane, perfluoropropanes, perfluorobutanes (e.g. perfluoro-n-butane, optionally in admixture with other isomers such as perfluoro-iso-butane), perfluoropentanes, perfluorohexanes or perfluoroheptanes; perfluoroalkenes such as perfluoropropene, perfluorobutenes (e.g. perfluorobut-2-ene), perfluorobutadiene, perfluoropentenes (e.g. perfluoropent-1-ene) or perfluoro-4-methylpent-2-ene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane or perfluorocycloheptane. Other halogenated gases include methyl chloride, fluorinated (e.g. perfluorinated) ketones such as perfluoroacetone and fluorinated (e.g. perfluorinated) ethers such as perfluorodiethyl ether. The use of perfluorinated gases, for example sulphur hexafluoride and perfluorocarbons such as perfluoropropane, perfluorobutanes, perfluoropentanes and perfluorohexanes, may be particularly advantageous in view of the recognised high stability in the bloodstream of microbubbles containing such gases. Other gases with physicochemical characteristics which cause them to form highly stable microbubbles in the bloodstream may likewise be useful.

Such dispersed gases may be administered in any convenient form, for example using any appropriate gas-containing ultrasound contrast agent formulation as the gas-containing composition. Representative examples of such formulations include microbubbles of gas stabilised (e.g. at least partially encapsulated) by a coalescence-resistant surface membrane (for example gelatin, e.g. as described in WO-A-8002365), a filmogenic protein (for example an albumin such as human serum albumin, e.g. as described in U.S. Pat. Nos. 4,718,433, 4,774,958, 4,844,882, EP-A-0359246, WO-A-9112823, WO-A-9205806, WO-A-9217213, WO-A-9406477 or WO-A-9501187), a polymer material (for example a synthetic biodegradable polymer as described in EP-A-0398935, an elastic interfacial synthetic polymer membrane as described in EP-A-0458745, a microparticulate biodegradable polyaldehyde as described in EP-A-0441468, a microparticulate N-dicarboxylic acid derivative of a polyamino acid-polycyclic imide as described in EP-A-0458079, or a biodegradable polymer as described in WO-A-9317718 or WO-A-9607434), a non-polymeric and non-polymerisable wall-forming material (for example as described in WO-A-9521631), or a surfactant (for example a polyoxyethylene-polyoxypropylene block copolymer surfactant such as a Pluronic, a polymer surfactant as described in WO-A-9506518, or a film-forming surfactant such as a phospholipid, e.g. as described in WO-A-9211873, WO-A-9217212, WO-A-9222247, WO-A-9428780, WO-A-9503835 or WO-A-9729783).

Other useful gas-containing contrast agent formulations include gas-containing solid systems, for example microparticles (especially aggregates of microparticles) having gas contained therewithin or otherwise associated therewith (for example being adsorbed on the surface thereof and/or contained within voids, cavities or pores therein, e.g. as described in EP-A-0122624, EP-A-0123235, EP-A-0365467, WO-A-9221382, WO-A-9300930, WO-A-9313802, WO-A-9313808 or WO-A-9313809). It will be appreciated that the echogenicity of such microparticulate contrast agents may derive directly from the contained/associated gas and/or from gas (e.g. microbubbles) liberated from the solid material (e.g. upon dissolution of the microparticulate structure).

The disclosures of all of the above-described documents relating to gas-containing contrast agent formulations are incorporated herein by reference.

Gas microbubbles and other gas-containing materials such as microparticles preferably have an initial average size not exceeding 10 μm (e.g. of 7 μm or less) in order to permit their free passage through the pulmonary system following administration, e.g. by intravenous injection. However, larger microbubbles may be employed where, for example, these contain a mixture of one or more relatively blood-soluble or otherwise diffusible gases such as air, oxygen, nitrogen or carbon dioxide with one or more substantially insoluble and non-diffusible gases such as perfluorocarbons. Outward diffusion of the soluble/diffusible gas content following administration will cause such microbubbles rapidly to shrink to a size which will be determined by the amount of insoluble/non-diffusible gas present and which may be selected to permit passage of the resulting microbubbles through the lung capillaries of the pulmonary system.

Where phospholipid-containing compositions are employed in accordance with the invention, e.g. in the form of phospholipid-stabilised gas microbubbles, representative examples of useful phospholipids include lecithins (i.e. phosphatidylcholines), for example natural lecithins such as egg yolk lecithin or soya bean lecithin, semisynthetic (e.g. partially or fully hydrogenated) lecithins and synthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; cardiolipins; sphingomyelins; fluorinated analogues of any of the foregoing; mixtures of any of the foregoing and mixtures with other lipids such as cholesterol. The use of phospholipids predominantly (e.g. at least 75%) comprising molecules individually bearing net overall charge, e.g. negative charge, for example as in naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and/or cardiolipins, for example as described in WO-A-9729783, may be particularly advantageous.

Representative examples of gas-containing microparticles materials which may be useful in accordance with the invention include carbohydrates (for example hexoses such as glucose, fructose or galactose; disaccharides such as sucrose, lactose or maltose; pentoses such as arabinose, xylose or ribose; α-, β- and γ-cyclodextrins; polysaccharides such as starch, hydroxyethyl starch, amylose, amylopectin, glycogen, inulin, pulullan, dextran, carboxymethyl dextran, dextran phosphate, ketodextran, aminoethyldextran, alginates, chitin, chitosan, hyaluronic acid or heparin; and sugar alcohols, including alditols such as mannitol or sorbitol), inorganic salts (e.g. sodium chloride), organic salts (e.g. sodium citrate, sodium acetate or sodium tartrate), X-ray contrast agents (e.g. any of the commercially available carboxylic acid and non-ionic amide contrast agents typically containing at least one 2,4,6-triiodophenyl group having substituents such as carboxyl, carbamoyl, N-alkylcarbamoyl, N-hydroxyalkylcarbamoyl, acylamino, N-alkylacylamino or acylaminomethyl at the 3- and/or 5-positions, as in metrizoic acid, diatrizoic acid, iothalamic acid, ioxaglic acid, iohexol, iopentol, iopamidol, iodixanol, iopromide, metrizamide, iodipamide, meglumine iodipamide, meglumine acetrizoate and meglumine diatrizoate), and polypeptides and proteins (e.g. gelatin or albumin such as human serum albumin).

In a further embodiment of the invention, vasoactive substances such as vasodilators, vasoconstrictors, hormones, local signal substances and receptor blockers, may be administered to induce vasomodification in the target tissue, for example to differentiate or characterize abnormalities such as lesions or tumours.

The following non-limitative examples serve to illustrate the invention.

EXAMPLE 1

In vivo power Doppler imaging of normal dog kidney 0.1 ml of a contrast agent comprising an aqueous dispersion of perfluorobutane microbubbles stabilised by hydrogenated egg phosphatidylserine, e.g. prepared as described in Example 4 of WO-A-9729783, was intravenously injected into an anaesthetised dog. One kidney was continuously imaged during and for 60 seconds after injection, using fundamental power Doppler imaging on an ATL HDI 3000 ultrasound scanner with the low velocity reject filter (wall filter) set to "medium" so as to display Doppler signals in respect of medium and high velocities only. The images were recorded on videotape with a frame rate of 25 frames/second. When the contrast agent reached the kidney an increase in the intensity of the power Doppler signal was observed, and the renal arteries were clearly visualised all the way out to the renal cortex. The signal intensity, particularly in respect of signals from small arteries in the renal cortex, was observed to pulse synchronously with the heart rate.

Intensities of the power Doppler signals were digitised from 256 successive frames of the videotape, thereby generating a two dimensional Doppler intensity image in which each pixel derived from a sequence of 256 time samples with a time step of 40 ms. The average intensity levels for each time series were subtracted, a Welch window was used on the data set along the time axis and a fast Fourier transform was performed to generate the power spectrum and phase spectrum of the original data. A new image was created by letting power at the heart frequency represent intensity and assigning a colour map to the phase so that the colour of the image was determined by the phase in each pixel. This image showed that the phase of the cardiac-synchronous pulsations was equal for all regions of the renal cortex and the larger renal arteries.

EXAMPLE 2

In vivo power Doppler imaging of dog kidney with renal arterial stenosis

A mild renal arterial stenosis was generated in an anaesthetised dog by partially occluding a branch of the renal artery. The occluder was set to produce an initial flow reduction of approximately 50% as measured by a transit time ultrasonic flow meter; substantially normal flow was restored after a few minutes as a result of autoregulation. 0.1 ml of a contrast agent comprising an aqueous dispersion of perfluorobutane microbubbles stabilised by hydrogenated egg phosphatidylserine, e.g. prepared as described in Example 4 of WO-A-9729783, was injected intravenously and power Doppler images were recorded and processed as described in Example 1. Despite the existence of normal blood flow in all regions of the kidney, the vascular bed affected by the stenosis was visualised in the final image as a region of different colour compared to the normal vascular bed, as a result of a phase shift caused by increased arterial resistance and by increased vascular compliance distal to the partial occlusion.

EXAMPLE 3

In vivo power Doppler imaging of metastatic lesions in human liver

The liver of a human subject with known cancer of the colon with metastatic liver lesions is imaged by harmonic power Doppler ultrasound. The instrument is adjusted for a high frame rate with no image persistence. The subject's ECG is recorded simultaneously. A bolus of the ultrasound contrast agent described in Example 1 (0.03 μl microbubbles/kg) is then injected, and a 10 second sequence of ultrasound images is recorded by digital means in the steady-state blood pool recirculation phase of the contrast agent. The images are analysed by extracting the exact frequency and phase of the heart rate from the ECG r-waves, and calculating the discrete complex Fourier coefficient at this frequency for temporal variations in brightness for each pixel in the image. A new image is then calculated, where local brightness is derived from the magnitude of the Fourier coefficient, and colour is derived from the phase. Due to the dominant arterial supply, the metastatic lesions are visible in this image as regions of enhanced pulsation amplitude (brighter). The colour of the lesions are different compared to the surrounding normal liver parenchyma due to differences in microvascular resistance and compliance between the tissues.

EXAMPLE 4

In vivo second harmonic B-mode imaging of metastatic lesions in human liver

The procedure of Example 3 is repeated except that the ultrasound scanner is set to operate in second harmonic B-mode. The images are analysed in the same manner as in Example 3, using the regional brightness variations caused by the heartbeats as input to the calculations of Fourier coefficients. The appearance of the lesions is similar to that observed in Example 3.

EXAMPLE 5

Power Doppler imaging of the prostate in a human subject with prostate cancer

A human subject with known prostatic carcinoma is imaged by harmonic power Dopper ultrasound. The instrument is adjusted for a high frame rate with no image persistence. The subject's ECG is recorded simultaneously. A bolus of the contrast agent described in Example 1 (0.03 μl microbubbles/kg) is then injected, and a 10 second sequence of ultrasound images is recorded by digital means in the steady state blood pool recirculation phase of the contrast agent. The images are analysed by extracting the exact frequency and phase of the heart rate from the ECG r-waves, and calculating the discrete complex Fourier coefficient at this frequency for the temporal variations in brightness for each pixel in the image. A new image is then calculated, where local brightness is derived from the magnitude of the Fourier coefficient, and colour is derived from the phase. The brightness and the colour of the lesions will differ from the surrounding normal prostate tissue due to differences in microvascular resistance and compliance between the tissues.

What is claimed is:

1. A method for detecting local aberrations in the perfusion and/or compliance of vasculated tissue within a human or non-human animal subject pretreated with an intravascularly administered ultrasound contrast agent, said method comprising the steps:

i) generating a sequence of ultrasound image data in respect of a region of interest in said vasculated tissue;

ii) processing said data sequence to generate waveforms representative of arterial pulsatility; and iii) analysing said waveforms for variations characteristic of local aberrations in tissue perfusion and/or compliance.

2. A method as claimed in claim 1 wherein the ultrasound image data sequence is generated by power Doppler imaging.

3. A method as claimed in claim 2 wherein the ultrasound image data sequence is processed by high-pass filtering at a threshold such that a pulsatile pattern is generated as arterial blood velocity varies above and below said threshold.

4. A method as claimed in claim 1 wherein the ultrasound image data sequence is processed with respect to a frequency and phase reference.

5. A method as claimed in claim 4 wherein said frequency and phase reference is a cardiac-synchronous signal.

6. A method as claimed in claim 4 wherein the ultrasound image data sequence is processed to generate phase information and phase shift detection is employed to identify potential local aberrations in perfusion and/or compliance in vasculated tissue in said region of interest.

7. A method as claimed in claim 4 wherein the ultrasound image data sequence is generated by power Doppler imaging.

8. A method as claimed in claim 4 wherein the ultrasound image data sequence is generated by B-mode imaging.

9. A method as claimed in claim 7 wherein the ultrasound image data sequence is generated by fundamental, harmonic or pulse inversion imaging.

10. A method as claimed in claim 1 which is combined with three dimensional acquisition and reconstruction of an ultrasound image.

11. A method as claimed in claim 1 wherein the intravascularly administered ultrasound contrast agent comprises a biocompatible gas.

12. A method as claimed in claim 11 wherein said gas comprises a sulphur halide or a perfluorocarbon.

13. A method as claimed in claim 12 wherein said gas comprises perfluorobutane.

14. A method as claimed in claim 11 wherein said gas is stabilised by amphiphilic lipid material.

15. A method as claimed in claim 14 wherein said amphiphilic lipid material comprises a membrane-forming lipid.

16. A method as claimed in claim 15 wherein said membrane-forming lipid comprises a phospholipid.

17. A method as claimed in claim 15 wherein at least 75% of said membrane-forming lipid comprises negatively charged phospholipid.

18. A method as claimed in claim 17 wherein said negatively charged phsopholipid comprises at least one phosphatidylserine.

\* \* \* \* \*